United States Patent
Menard-Szczebara et al.

(10) Patent No.: US 11,752,079 B2
(45) Date of Patent: Sep. 12, 2023

(54) ANTIMICROBIAL MIXTURE CONTAINING 4-(3-ETHOXY-4-HYDROXYPHENYL)BUTAN-2-ONE AND A DIOL, AND COSMETIC COMPOSITION CONTAINING SAME

(71) Applicant: L'OREAL, Paris (FR)

(72) Inventors: Florence Menard-Szczebara, Chevilly Larue (FR); Sylvie Cupferman, Chevilly Larue (FR); Julien Galvan, Chevilly Larue (FR); Véronique Chevalier, Chevilly Larue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/626,051

(22) PCT Filed: Jun. 27, 2018

(86) PCT No.: PCT/EP2018/067298
§ 371 (c)(1),
(2) Date: Dec. 23, 2019

(87) PCT Pub. No.: WO2019/002392
PCT Pub. Date: Jan. 3, 2019

(65) Prior Publication Data
US 2021/0205192 A1     Jul. 8, 2021

(30) Foreign Application Priority Data

Jun. 30, 2017 (FR) ........................ 1756159
Jun. 30, 2017 (FR) ........................ 1756165
Nov. 10, 2017 (FR) ........................ 1760568

(51) Int. Cl.
| | | |
|---|---|---|
| A61K 8/35 | (2006.01) | |
| A61K 8/34 | (2006.01) | |
| A61K 8/06 | (2006.01) | |
| A61Q 19/00 | (2006.01) | |

(52) U.S. Cl.
CPC ............ *A61K 8/35* (2013.01); *A61K 8/062* (2013.01); *A61K 8/345* (2013.01); *A61Q 19/00* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 2012/0251460 A1 | 10/2012 | Dalko | |
| 2014/0057991 A1* | 2/2014 | Chevalier | ............... A61Q 5/00 514/678 |

FOREIGN PATENT DOCUMENTS

| | | |
|---|---|---|
| EP | 1 206 933 A1 | 5/2002 |
| FR | 2 973 227 A1 | 10/2012 |
| JP | 2005-015401 A | 1/2005 |
| JP | 2006-343492 A | 12/2006 |
| JP | 2010-209116 A | 9/2010 |
| WO | WO 03/069994 A1 | 8/2003 |
| WO | WO 2008/135085 | 11/2008 |
| WO | WO 2011/039445 A1 | 4/2011 |
| WO | WO 2012/130953 A1 | 10/2012 |

OTHER PUBLICATIONS

J. Jänichen.: The Quest for the Ideal Preserving System—Reducing traditional Preservatives in Combination with Dermasoft Octiol, Euro-Cosmetics Jul./Aug. 2004, vol. n° 12, pp. 10 to 16.
F.C. Kull, P.C. Eisman, H.D. Sylwestrowka, and R.L. Mayer, *Mixtures of Quaternary Ammonium Compounds and Long Chain Fatty Acids as Antifungal Agents*, Applied Microbiology 9:538-541, 1961.
Opposition filed Thor GmbH dated Nov. 22, 2021 against EP 3 644 734 B1, European counterpart to this application.

* cited by examiner

*Primary Examiner* — Jennifer A Berrios
(74) *Attorney, Agent, or Firm* — POLSINELLI PC

(57) ABSTRACT

The invention relates to an antimicrobial mixture containing 4-(3-ethoxy-4-hydroxy-phenyl)butan-2-one and a diol compound chosen from 1,3-propanediol, 1,2-octane-diol and 1,2-decanediol, and also to a cosmetic composition containing such a mixture. Use in caring for, making up and cleansing keratin materials.

15 Claims, No Drawings

ANTIMICROBIAL MIXTURE CONTAINING 4-(3-ETHOXY-4-HYDROXYPHENYL)BUTAN-2-ONE AND A DIOL, AND COSMETIC COMPOSITION CONTAINING SAME

CROSS REFERENCE TO RELATED APPLICATIONS

This application is a National Phase filing under 35 U.S.C. § 371 of PCT/EP2018/067298 filed on 27 Jun. 2018; which application in turn claims priority to Application No. 1756159 filed in France on 30 Jun. 2017; Application No. 1756165 filed in France on 30 Jun. 2017; and Application No. 1760568 filed in France on 10 Nov. 2017. The entire contents of each application are hereby incorporated by reference.

The subject of the present invention is an antibacterial mixture containing 4-(3-ethoxy-4-hydroxyphenyl)butan-2-one and a particular diol compound, and also a cosmetic composition containing such a mixture.

4-(3-Ethoxy-4-hydroxyphenyl)butan-2-one (ketone compound) is an interesting substance as a preserving agent for cosmetic compositions, for protecting the compositions against microbial contamination, as described in the application WO 2011/039445.

However, it is desirable to be able to incorporate said ketone compound in reduced concentration in compositions, especially cosmetic or dermatological compositions, while at the same time maintaining good antimicrobial conservation performance. Combinations of the ketone compound with other compounds that have antimicrobial efficacy are thus sought for this purpose.

The inventors have discovered, unexpectedly, that the combination of 4-(3-ethoxy-4-hydroxyphenyl)butan-2-one with a diol compound chosen from 1,3-propanediol, 1,2-octanediol and 1,2-decanediol makes it possible to obtain an antimicrobial mixture which has synergistic antimicrobial activity.

The results of the examples described below show the synergistic antimicrobial activity obtained with the minimum inhibitory concentration (MIC) measurements taken with several mixtures. The antimicrobial activity is considered as being synergistic when the antimicrobial mixture makes it possible to obtain a percentage of strain growth of less than or equal to 20%, or even less than or equal to 25%.

The combination of 4-(3-ethoxy-4-hydroxyphenyl)butan-2-one with 1,3-propanediol in particular weight ratios makes it possible to obtain an antimicrobial mixture with synergistic antimicrobial activity, in particular on moulds, in particular on *Aspergillus niger*.

Application FR-A-2973227 describes a cosmetic composition containing 4-(3-ethoxy-4-hydroxyphenyl)butan-2-one and a particular hydrophilic solvent including 1,3-propanediol. Said solvent makes it possible to dissolve the ketone compound. This document does not describe any antimicrobial property for the mixture described.

The combination of 4-(3-ethoxy-4-hydroxyphenyl)butan-2-one with 1,2-octanediol makes it possible to obtain an antimicrobial mixture with synergistic antimicrobial activity, in particular on yeasts, in particular on *Candida albicans*.

Application FR-A-2962333 describes a cosmetic composition for the treatment of oily skin comprising a 2-alkoxy-4-alkyl ketone phenol and an essential oil. The composition may comprise an additional active agent for oily skin care, such as antimicrobial agents, among which mention is made of caprylyl glycol. This document does not specifically describe an antimicrobial mixture constituted of the combination of 4-(3-ethoxy-4-hydroxyphenyl)butan-2-one with 1,2-octanediol, nor does it suggest that such a mixture has synergistic antimicrobial activity on yeasts, in particular on *Candida albicans*.

The combination of 4-(3-ethoxy-4-hydroxyphenyl)butan-2-one with 1,2-decanediol makes it possible to obtain an antimicrobial mixture which has synergistic antimicrobial activity, in particular on moulds, in particular on *Aspergillus niger*, and on yeasts, in particular on *Candida albicans*.

More specifically, a subject of the invention is an antimicrobial mixture comprising, or constituted of, 4-(3-ethoxy-4-hydroxyphenyl)butan-2-one and a diol compound chosen from 1,3-propanediol, 1,2-octanediol and 1,2-decanediol, and when the diol is 1,3-propanediol, the latter is present in a 4-(3-ethoxy-4-hydroxyphenyl)butan-2-one/1,3-propanediol weight ratio ranging from 0.02 to 0.15.

A subject of the invention is also a composition, especially a cosmetic or dermatological composition, comprising, in a physiologically acceptable medium, said mixture described previously.

A further subject of the invention is a process for the non-therapeutic cosmetic treatment of keratin materials, comprising the application to the keratin materials of a composition as described previously. The process may be a cosmetic process for caring for or making up or cleansing keratin materials.

A subject of the invention is also a process for conserving a composition comprising a physiologically acceptable medium, in particular a cosmetic or dermatological composition, characterized in that it consists in incorporating into said composition an antimicrobial mixture as described previously.

A subject of the invention is also the use of the antimicrobial mixture described previously for conserving a composition comprising a physiologically acceptable medium.

4-(3-Ethoxy-4-hydroxyphenyl)butan-2-one is a compound of formula:

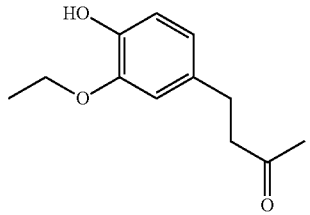

According to a first embodiment, a subject of the invention is an antimicrobial mixture comprising, or constituted of, 4-(3-ethoxy-4-hydroxyphenyl)butan-2-one and 1,3-propanediol present in amounts such that the 4-(3-ethoxy-4-hydroxyphenyl)butan-2-one/1,3-propanediol weight ratio ranges from 0.02 to 0.15.

Advantageously, 4-(3-ethoxy-4-hydroxyphenyl)butan-2-one and 1,3-propanediol are present in said mixture in a content such that the 4-(3-ethoxy-4-hydroxyphenyl)butan-2-one/1,3-propanediol weight ratio ranges from 0.02 to 0.07.

According to a second embodiment, a subject of the invention is an antimicrobial mixture comprising, or constituted of, 4-(3-ethoxy-4-hydroxyphenyl)butan-2-one and 1,2-octanediol.

1,2-Octanediol corresponds to the compound caprylyl glycol (CAS No.: 1117-86-8).

Advantageously, 4-(3-ethoxy-4-hydroxyphenyl)butan-2-one and 1,2-octanediol are present in said mixture in a content such that the 4-(3-ethoxy-4-hydroxyphenyl)butan-2-one/1,2-octanediol weight ratio ranges from 0.1 to 1.5, preferably ranges from 0.2 to 1.1.

According to a third embodiment, a subject of the invention is an antimicrobial mixture comprising, or constituted of, 4-(3-ethoxy-4-hydroxyphenyl)butan-2-one and 1,2-decanediol.

Advantageously, 4-(3-ethoxy-4-hydroxyphenyl)butan-2-one and 1,2-decanediol are present in said mixture in a content such that the 4-(3-ethoxy-4-hydroxyphenyl)butan-2-one/1,2-decanediol weight ratio ranges from 1.6 to 12, preferably ranges from 1.6 to 10 and preferentially ranges from 2.8 to 9.

The antimicrobial mixture may have a 4-(3-ethoxy-4-hydroxyphenyl)butan-2-one/1,2-decanediol weight ratio ranging from 1.6 to 6.4, preferably ranging from 1.6 to 4.8, preferentially ranging from 2.8 to 6.4 and more preferentially ranging from 2.8 to 4.8. Such a mixture has good antimicrobial activity on moulds, especially on Aspergillus niger.

The antimicrobial mixture may have a 4-(3-ethoxy-4-hydroxyphenyl)butan-2-one/1,2-decanediol weight ratio ranging from 2.8 to 12, preferably ranging from 3.2 to 10, in particular ranging from 3.5 to 9, preferentially ranging from 6 to 12, more preferentially ranging from 6 to 10, in particular ranging from 6 to 9. Such a mixture has good antimicrobial activity on yeasts, in particular on Candida albicans.

The compound 4-(3-ethoxy-4-hydroxyphenyl)butan-2-one may be present in the composition according to the invention in an amount ranging from 0.01% to 5% by weight relative to the total weight of the composition, preferably ranging from 0.01% to 3% by weight, preferentially ranging from 0.01% to 2.5% by weight and more preferentially ranging from 0.01% to 2% by weight.

A subject of the invention is also a composition comprising, in a physiologically acceptable medium, the antimicrobial mixture described previously.

The term "physiologically acceptable medium" is intended to mean a medium that is compatible with human keratin materials such as the skin, the scalp, the hair and the nails. Said medium may comprise one or more additional ingredients other than the ketone compound and the diol described previously.

The composition may comprise at least one additional ingredient chosen from water, oils, polyols containing from 2 to 10 carbon atoms, gelling agents, surfactants, film-forming polymers, colorants, fragrances, fillers, UV-screening agents, plant extracts, cosmetic and dermatological active agents, and salts.

The composition according to the invention may comprise an aqueous phase.

The composition may comprise water, which may be present at a content ranging from 5% to 90% by weight relative to the total weight of the composition, and preferably ranging from 35% to 75% by weight.

The composition may also comprise a polyol that is water-miscible at ambient temperature (25° C.), especially chosen from polyols especially containing from 2 to 10 carbon atoms, preferably containing from 2 to 6 carbon atoms, such as glycerol, propylene glycol, 1,3-propanediol, butylene glycol, pentylene glycol, hexylene glycol, dipropylene glycol, diethylene glycol or diglycerol.

The compositions according to the invention may be in the form of oil-in-water (O/W) emulsions, water-in-oil (W/O) emulsions or multiple emulsions (triple: W/O/W or O/W/O), oily solutions, oily gels, aqueous solutions, aqueous gels, solid compositions. These compositions are prepared according to the usual methods.

The compositions according to the invention may be more or less fluid and may have the appearance of a white or coloured cream, an ointment, a milk, a lotion, a serum, a paste or a foam. They may be optionally applied to the skin in aerosol form. They may also be in solid form, for example in the form of a stick or a compact powder.

The composition according to the invention may especially be in the form of:
- a makeup product, especially for making up the skin of the face, the body, or the lips or the eyelashes;
- an aftershave gel or lotion; a shaving product;
- a deodorant (stick, roll-on or aerosol);
- a hair-removing cream;
- a body hygiene composition such as a shower gel or a shampoo;
- a pharmaceutical composition;
- a solid composition such as a soap or a cleansing bar;
- an aerosol composition also comprising a pressurized propellant;
- a hairsetting lotion, a hair-styling cream or gel, a dye composition, a permanent-waving composition, a lotion or a gel for combating hair loss, or a hair conditioner;
- a composition for caring for or cleansing the skin.

A subject of the invention is also a process for preparing a composition, especially a cosmetic or dermatological composition, comprising a step of mixing 4-(3-ethoxy-4-hydroxyphenyl)butan-2-one, the diol described previously, and one or more additional ingredients, especially cosmetic or dermatological ingredients, such as those described previously.

The invention is illustrated in greater detail in the example that follows. The amounts of the ingredients are expressed as weight percentages.

Example 1: Determination of the Synergistic Antimicrobial Activity as MIC

The demonstration of a synergistic antimicrobial activity effect with a mixture of 4-(3-ethoxy-4-hydroxyphenyl)butan-2-one (referred to as substance A) and of a diol (referred to as substance B) is performed by calculating the synergy index (or FIC index) according to the following formula:

$$\text{FIC Index} = (\text{MICa with B}/\text{MICa}) + (\text{MICb with A}/\text{MICb})$$

with.
- MICa with B: minimum concentration of product A in the combination A+B which makes it possible to obtain an inhibitory effect
- MICb with A: minimum concentration of product B in the combination A+B which makes it possible to obtain an inhibitory effect.
- MICa: minimum inhibitory concentration of product A alone.
- MICb: minimum inhibitory concentration of product B alone.

This formula was described for the first time in the article by F. C. Kull, P. C. Eisman, H. D. Sylwestrowka, and R. L. Mayer, Applied Microbiology 9:538-541, 1961.

For each compound tested alone, the MIC is considered as the first concentration which makes it possible to obtain a microbial growth percentage of less than or equal to 20%.

As regards the combinations tested, MICa with b and MICb with a are the respective concentrations of A and of B in the combinations which make it possible to obtain a microbial growth percentage of less than or equal to 20%.

Interpretation of the FIC Index:

When the FIC index value is less than or equal to 1, it is considered that the combination of test compounds has a synergistic effect.

The results obtained are summarized in the following tables.

The combination of compounds A and B was tested on the following strains: *Aspergillus niger* and/or *Candida albicans*.

The microbial strain *Aspergillus niger* ATCC 6275, and a double-concentration Sabouraud broth liquid culture medium supplemented with polyoxyethylenated (20 OE) sorbitan monopalmitate (Tween 40 from Croda) and Phytagel© BioReagent were used (i.e. a mixture of 5 g of Phytagel+0.6 g Tween 40+60 g of Sabouraud broth).

The microbial strain *Candida albicans* ATCC 10231 and a double-concentration Sabouraud broth liquid culture medium were used.

A 96-well microplate and an incubation time of 32.5° C. are used.

The incubation time of the microplate is:

from 18 to 24 h under aerobic conditions for *Candida albicans* ATCC 10231;

from 24 to 30 h under aerobic conditions for *Aspergillus niger* ATCC 6275.

Test

For Each Compound:

A=4-(3-ethoxy-4-hydroxyphenyl)-2-butanone compound

B=diol compound.

A 10% (weight/volume) stock solution was prepared by mixing 1 g of compound in 9 ml of aqueous 1% o agar solution. Successive dilutions were made with the 1% o agar solution.

Test of compounds A and B alone

50 µl of each of the daughter solutions obtained containing compound A or B are added to the microplate wells. 100 µl of Sabouraud liquid nutrient broth inoculated with the strain *Aspergillus niger* and 50 µl of aqueous 1% o agar solution are also added thereto.

Test of compounds A and B as a mixture

50 µl of each of the daughter solutions obtained containing compound A and 50 µl of each of the daughter solutions obtained containing compound B are added to the microplate wells. 100 µl of Sabouraud liquid nutrient broth inoculated at double concentration with the strain *Aspergillus niger* are also added thereto.

Microbial Growth Control

A positive microbial growth control was also prepared. The positive microbial growth control corresponds to a mixture of 100 µl of aqueous 1% o agar solution with 100 µl of Sabouraud liquid nutrient broth inoculated at double concentration with the strain *Aspergillus niger* in the absence of compounds A and B.

Absorbance Control of Compounds A and B Alone

An absorbance control was performed in parallel on compounds A and B alone. This control corresponds to 100 µl of double concentration sterile Sabouraud liquid nutrient broth+100 µl of double concentration compound A or B.

In the three cases (absorbance control, growth control and test), the final volume present in each of the microplate wells is 200 µl.

In the two cases (test and control), the inoculum represents the concentration of the *Aspergillus niger* strain present in the final volume of the wells (200 µl) and is between 2 and 6×10$^5$ cfu/ml of *Aspergillus niger*.

The minimum inhibitory concentration (MIC) of each compound A and B alone and in combination was determined by means of optical density measurements at a wavelength of 620 nm.

The test as described above (tests, absorbance control and growth control) was performed again to test the combination A and B on the *Candida albicans* strain.

The following results were obtained with compound B1=1,3-propanediol:

| *Aspergillus Niger* | | | | |
|---|---|---|---|---|
| | concentrations tested (in weight %) | | | |
| | 0 A | 0.025 A | 0.05 A | 0.1 A |
| 0 B1 | | 42 | 25 | 10 |
| 0.125 B1 | 77 | 37 | 24 | 6 |
| 0.25 B1 | 62 | 27 | 12 (FIC 0.63) | 6 |
| 0.5 B1 | 50 | 25 | 10 (FIC 0.75) | 9 |
| 1 B1 | 36 | 6 (FIC 0.75) | 5 (FIC 1) | 8 |
| 2 B1 | 11 | 10 | −8 | 5 |

| % MIC of A alone | % MIC of B1 alone | MIC of compound each as a mixture | | FIC Index | |
|---|---|---|---|---|---|
| | | A % | B1 % | | |
| 0.1 | 2 | 0.025 | 1 | 0.75 Synergy | Ratio A/B1 = 2 |

The results obtained show synergistic inhibitory activity for the mixtures:

i) 0.025% of A and 1% of B1, i.e. ratio A/B1=0.025
ii) 0.05% of A and 1% of B1, i.e. ratio A/B1=0.05
iii) 0.05% of A and 0.5% of B1, i.e. ratio A/B1=0.1
iv) 0.05% of A and 0.25% of B1, i.e. ratio A/B1=0.2

Example 2: Determination of the Synergistic Antimicrobial Activity in MIC on the Microbial Strain *Candida albicans*

The demonstration of a synergistic antimicrobial activity effect with a mixture of 4-(3-ethoxy-4-hydroxyphenyl)butan-2-one (referred to as substance A) and of 1,2-octanediol (referred to as substance B2) is performed according to the protocol in Example 1, on the *Candida albicans* strain.

The following results were obtained:

| | concentrations tested (in weight %) | | | | |
|---|---|---|---|---|---|
| | 0 A | 0.025 A | 0.05 A | 0.1 A | 0.2 A |
| 0 B2 | | 81 | 60 | 27 | 4 |
| 0.025 B2 | 79 | 72 | 46 | 16 (FIC 0.63) | 2 |

-continued

| | concentrations tested (in weight %) | | | | |
|---|---|---|---|---|---|
| | 0 A | 0.025 A | 0.05 A | 0.1 A | 0.2 A |
| 0.05 B2 | 60 | 41 | 24 (FIC 0.5) | 8 (FIC 0.75) | 2 |
| 0.1 B2 | 23 | 10 (FIC 0.63) | 6 (FIC 0.75) | 1 (FIC 1) | 0 |
| 0.2 B2 | 0 | 0 | 0 | 0 | 0 |

| % MIC A | MIC B2 | MIC of compound each as a mixture A % | B2 % | FIC Index | |
|---|---|---|---|---|---|
| 0.2 | 0.2 | 0.025 | 0.1 | 0.63 | Ratio A/B2 = 0.25 |

The results obtained show synergistic inhibitory activity for the mixtures:
i) 0.025% of A and 0.1% of B2, i.e. ratio A/B2=0.25
ii) 0.05% of A and 0.1% of B2, i.e. ratio A/B2=0.5
iii) 0.1% of A and 0.1% of B2, i.e. ratio A/B2=1
iv) 0.05% of A and 0.05% of B2, i.e. ratio A/B2=1
v) 0.1% of A and 0.05% of B2, i.e. ratio A/B2=2
vi) 0.1% of A and 0.025% of B2, i.e. ratio A/B2=4

Example 3: Determination of the Antimicrobial Activity of the Antimicrobial Mixture The antimicrobial efficacy of the 4-(3-ethoxy-4-hydroxyphenyl)butan-2-one+1,2-octanediol antimicrobial mixture (respective weight ratio of 0.1) was evaluated by the Challenge Test method.

Protocol

The method of the challenge test is constituted of an artificial contamination of the sample with microbial strains from collection (bacteria, yeasts and moulds) and of an evaluation of the number of revivable microorganisms seven days after inoculation.

In order to demonstrate the effect of the antimicrobial mixture, the antimicrobial activity of a cosmetic formula containing 0.05% of 4-(3-ethoxy-4-hydroxyphenyl)butan-2-one and 0.5% of 1,2-octanediol was compared with the same formula alone (control), after inoculation with about $10^6$ CFU (colony-forming units)/gram of cosmetic formulation.

Cosmetic Formula

A facial care oil-in-water emulsion having the following composition was prepared (contents in weight percentages):

| | |
|---|---|
| Sorbitan tristearate (Span 65 V from Croda) | 0.9% |
| Glyceryl mono/distearate (36/64)/potassium stearate mixture (Tegin Pellets from Goldschmidt) | 3% |
| Polyethylene glycol stearate (40 ethylene oxide units) | 2% |
| 4-(3-Ethoxy-4-hydroxyphenyl)butan-2-one | 0.05% |
| 1,2-Octanediol | 0.2% |
| 1,3-Propanediol | 2% |
| Mineral oil, microcrystalline wax and paraffin (Vaseline Blanche Codex 236 from Aiglon) | 4% |
| Liquid fraction of shea butter (Shea Olein from Olvea) | 1% |
| Cyclopentadimethylsiloxane | 5% |
| Cetyl alcohol | 4% |
| Apricot kernel oil | 0.3% |
| Hydrogenated polyisobutene (Parleam from NOF Corporation) | 7.2% |
| Myristyl myristate | 2% |
| Stearic acid | 1.2% |
| Caffeine | 0.1% |
| Citric acid | 0.2% |
| Glycerol | 3% |
| Sodium hydroxide | 0.05% |
| Water q.s. | 100% |

Microorganism Cultures 5 pure cultures of microorganisms were used.

| MICROORGANISMS | Subculturing medium | T° | ATCC |
|---|---|---|---|
| Escherichia coli (Ec) | Trypto-casein soya | 35° C. | 8739 |
| Enterococcus faecalis (Ef) | Trypto-casein soya | 35° C. | 33186 |
| Pseudomonas aeruginosa (Pa) | Trypto-casein soya | 35° C. | 19429 |
| Candida albicans (Ca) | Sabouraud | 35° C. | 10231 |
| Aspergillus niger (An) | Malt | 35° C. | 6275 |

ATCC = American Type Culture Collection

The strains of gram-negative bacteria (Escherichia coli and Pseudomonas aeruginosa), gram-positive bacterium (Enterococcus faecalis), yeast (Candida albicans), and mould (Aspergillus niger) are inoculated into subculturing medium, respectively the day before inoculation for the bacteria and the yeast, and 5 days before inoculation for the mould.

On the Day of Inoculation:
a suspension in tryptone salt diluent is prepared, respectively, for the bacteria and the yeast, so as to obtain by spectrophotometer a suspension with an optical density of between 35% and 45% of transmitted light at 544 nm;
for the mould, the spores are collected by washing the agar with 6 to 7 ml of harvesting solution and the suspension is recovered in a sterile tube or flask.

After homogenizing the microbial suspension, 0.2 ml of inoculum is introduced into each pill bottle (the suspensions are used pure: between $1 \times 10^8$ and $3 \times 10^8$ CFU per ml) and the microbial suspension in the 20 g of product (=cosmetic formulation) is homogenized thoroughly using a spatula.

The content of microorganisms present in the product corresponds after homogenization to a concentration of $10^6$ microorganisms per gram of product, i.e. inoculation to 1% of an inoculum containing $10^8$ microorganisms per ml.

After 7 days of contact time between the microorganisms and the product at 22° C.±2° C. and in the dark, ten-fold dilutions are performed out and the number of revivable microorganisms remaining in the product is counted.

Results

| | No. of CFU/gram of product at T7 days | | | | |
|---|---|---|---|---|---|
| | E. coli | P. aeruginosa | E. faecalis | C. albicans | A. niger |
| Cosmetic formula | <200 | <200 | <200 | <200 | 8.4E4 |

<200 CFU: sensitivity threshold of the method

Example 4: Determination of the Synergistic Antimicrobial Activity as MIC

The demonstration of a synergistic antimicrobial activity effect with a mixture of 4-(3-ethoxy-4-hydroxyphenyl)butan-2-one (referred to as substance A) and of 1,2-decanediol (referred to as substance B3) is performed according to the protocol described in Example 1, using the *Aspergillus niger* and *Candida albicans* strains.

The Following Results were Obtained:

*Aspergillus niger*

| Concentrations tested (in weight %) | 0 A | 0.025 A | 0.05 A | 0.1 A |
|---|---|---|---|---|
| 0 B3 | | 39 | 32 | 12 |
| 0.0125 B3 | 42 | 17 (FIC 0.75) | 14 (FIC 1) | 11 |
| 0.025 B3 | 10 | 3 | 4 | 6 |

| % MIC of A alone | % MIC of B3 alone | MIC of each compound as a mixture A % | MIC of each compound as a mixture B3 % | FIC Index | Ratio A/B3 |
|---|---|---|---|---|---|
| 0.1 | 0.025 | 0.025 | 0.0125 | 0.75 | 2 |

The results obtained show synergistic inhibitory activity for the mixture:

i) 0.025% of A and 0.0125% of B3, i.e. ratio A/B3=2 ii) 0.05% of A and 0.0125% of B3, i.e. ratio A/B3=4

*Candida Albicans*

| | Concentrations tested (in weight %) | | | | |
|---|---|---|---|---|---|
| | 0 A | 0.025 A | 0.05 A | 0.1 A | 0.2 A |
| 0 B3 | | 78 | 61 | 25 | 3 |
| 0.0125 B3 | 45 | 34 | 18 (FIC 0.75) | 6 (FIC 1) | 1 |
| 0.025 B3 | 3 | 0 | 1 | 0 | 0 |

| % MIC of A alone | % MIC of B3 alone | MIC of each compound as a mixture A % | MIC of each compound as a mixture B3% | FIC Index | Ratio A/B3 |
|---|---|---|---|---|---|
| 0.2 | 0.025 | 0.05 | 0.0125 | 0.75 | 4 |

The results obtained show synergistic inhibitory activity for the mixtures:

i) 0.05% of A and 0.0125% of B3, i.e. ratio A/B3=4 ii) 0.1% of A and 0.0125% of B3, i.e. ratio A/B3=8

Example 5: Determination of the Antimicrobial Activity of the Antimicrobial Mixture The antimicrobial efficacy of the 4-(3-ethoxy-4-hydroxyphenyl)butan-2-one+with 1,3-propanediol (compound B1) antimicrobial mixture (respective weight ratio of 0.16) was evaluated by the Challenge Test method as described in the example 3.

Cosmetic Formula

A facial care oil-in-water emulsion having the following composition was prepared (contents in weight percentages):

| | |
|---|---|
| Sorbitan tristearate (Span 65 V from Croda) | 0.9% |
| Glyceryl mono/distearate (36/64)/potassium stearate mixture (Tegin Pellets from Goldschmidt) | 3% |
| Polyethylene glycol stearate (40 ethylene oxide units) | 2% |
| 4-(3-ethoxy-4-hydroxyphenyl)butan-2-one | 0.5% |
| 1,3-propanediol | 5% |
| Propane-1,3-diol | 2% |
| Mixture of mineral oil, microcrystalline wax and paraffin (Vaseline Blanche Codex 236 from Aiglon) | 4% |
| Liquid fraction of shea butter (Shea Olein from Olvea) | 1% |
| Cyclopentadimethylsiloxane | 5% |
| Cetyl alcohol | 4% |
| Apricot kernel oil | 0.3% |
| Hydrogenated polyisobutene (Parleam from NOF Corporation) | 7.2% |
| Myristyl myristate | 2% |
| Stearic acid | 1.2% |
| Caffeine | 0.1% |
| Glycerol | 3% |
| Sodium hydroxide | 0.05% |
| Water qs | 100% |

Results

| | No. of CFU/gram of product at T7 days | | | | |
|---|---|---|---|---|---|
| | E. coli | P. aeruginosa | E. faecalis | C. albicans | A. niger |
| Antimicrobial mixture | <200 | <200 | <200 | <200 | <200 |

<200 CFU: sensitivity threshold of the method

The invention claimed is:

1. An antimicrobial mixture comprising 4-(3-ethoxy-4-hydroxyphenyl)butan-2-one and 1,3-propanediol, wherein the 4-(3-ethoxy-4-hydroxyphenyl)butan-2-one and 1,3-propanediol are present in the mixture in an amount such that the 4-(3-ethoxy-4-hydroxyphenyl)butan-2-one/1,3-propanediol weight ratio ranges from 0.02 to 0.15 and wherein the antimicrobial mixture exhibits synergistic inhibitory activity.

2. The antimicrobial mixture according to claim 1, wherein said weight ratio ranges from 0.02 to 0.07.

3. A composition comprising, in a physiologically acceptable medium, an antimicrobial mixture according to claim 1.

4. The composition according to claim 3, which comprises at least one additional ingredient chosen from water, oils, polyols containing from 2 to 10 carbon atoms, gelling agents, surfactants, film-forming polymers, colorants, fragrances, fillers, UV-screening agents, plant extracts, cosmetic and dermatological active agents, and salts.

5. The composition according to claim 3, wherein the 4-(3-ethoxy-4-hydroxyphenyl)butan-2-one is present in a content ranging from 0.01% to 5% by weight relative to the total weight of the composition.

6. A method for the conservation of a composition comprising a physiologically acceptable medium which comprises including an antimicrobial mixture according to claim 1 in said composition.

7. The composition according to claim 3, wherein the 4-(3-ethoxy-4-hydroxyphenyl)butan-2-one is present in a content ranging from 0.01% to 5% by weight relative to the total weight of the composition and the weight ratio of the 4-(3-ethoxy-4-hydroxyphenyl)butan-2-one/1,3-propanediol ranges from 0.02 to 0.07.

8. The antimicrobial mixture according to claim 1, which exhibits synergistic inhibitory activity against moulds.

9. The antimicrobial mixture according to claim 1, which exhibits synergistic inhibitory activity against *Aspergillus niger*.

10. A composition comprising, in a physiologically acceptable medium, an antimicrobial mixture according to claim 9.

11. The composition according to claim 10, which comprises at least one additional ingredient chosen from water, oils, polyols containing from 2 to 10 carbon atoms, gelling agents, surfactants, film-forming polymers, colorants, fragrances, fillers, UV-screening agents, plant extracts, cosmetic and dermatological active agents, and salts.

12. The composition according to claim 10, wherein the 4-(3-ethoxy-4-hydroxyphenyl)butan-2-one is present in a content ranging from 0.01% to 5% by weight relative to the total weight of the composition.

13. A composition comprising, in a physiologically acceptable medium, an antimicrobial mixture according to claim 8.

14. The composition according to claim 13, which comprises at least one additional ingredient chosen from water, oils, polyols containing from 2 to 10 carbon atoms, gelling agents, surfactants, film-forming polymers, colorants, fragrances, fillers, UV-screening agents, plant extracts, cosmetic and dermatological active agents, and salts.

15. The composition according to claim 13, wherein the 4-(3-ethoxy-4-hydroxyphenyl)butan-2-one is present in a content ranging from 0.01% to 5% by weight relative to the total weight of the composition.

* * * * *